United States Patent
Chen (10) Patent No.: US 10,598,751 B1
(45) Date of Patent: Mar. 24, 2020

(54) SYSTEM AND METHOD FOR SEPARATION OF WATER AND FAT SIGNALS DURING SPIN-LOCK MAGNETIC RESONANCE IMAGING

(71) Applicant: THE CHINESE UNIVERSITY OF HONG KONG, Shatin, N.T., Hong Kong (CN)

(72) Inventor: Weitian Chen, Hong Kong (CN)

(73) Assignee: THE CHINESE UNIVERSITY OF HONG KONG, Shatin (HK)

( * ) Notice: Subject to any disclaimer, the term of this patent is extended or adjusted under 35 U.S.C. 154(b) by 0 days.

(21) Appl. No.: 16/267,218

(22) Filed: Feb. 4, 2019

(51) Int. Cl.
| G01R 33/54 | (2006.01) |
| G01R 33/565 | (2006.01) |
| G01R 33/50 | (2006.01) |
| G01R 33/44 | (2006.01) |

(52) U.S. Cl.
CPC ......... *G01R 33/543* (2013.01); *G01R 33/446* (2013.01); *G01R 33/50* (2013.01); *G01R 33/56563* (2013.01)

(58) Field of Classification Search
CPC ............ G01R 33/543; G01R 33/56563; G01R 33/446; G01R 33/50
See application file for complete search history.

(56) References Cited

U.S. PATENT DOCUMENTS

| 2011/0140696 A1* | 6/2011 | Yu ................. | G01R 33/4828 324/309 |
| 2018/0031661 A1* | 2/2018 | Chen ............... | A61B 5/055 |

OTHER PUBLICATIONS

Chen, Weitian. "Artifacts correction for T1rho imaging with constant amplitude spin-lock." Journal of Magnetic Resonance 274 (2017): 13-23.
Dixon, W. Thomas. "Simple proton spectroscopic imaging." Radiology 153, No. 1 (1984): 189-194.
Jiang, et al. "On-resonance and off-resonance continuous wave constant amplitude spin-lock and T1ρ quantification in the presence of B1 and B0 inhomogeneities." NMR in Biomedicine (2018): e3928.
Silver, et al. "Highly selective π2 and π pulse generation." Journal of Magnetic Resonance (1969) 59, No. 2 (1984): 347-351.
Weidlich et al., "In-Vivo water T2 mapping in tissues containing water and fat using a T2-prepared 3D Dixon TSE sequence and a pre-calibrated fat spectrum model," Proc. Intl. Soc. Mag. Reson. Med. 26 (2018) 4223. Accessed at http://indexsmart.mirasmart.com/ISMRM2018/PDFfiles/4223.html.

(Continued)

*Primary Examiner* — G. M. A Hyder
(74) *Attorney, Agent, or Firm* — Kilpatrick Townsend & Stockton LLP (57) ABSTRACT

Separation of fat and water signals in MRI images can be achieved by a technique that includes using a spin-lock RF pulse sequence that incorporates adiabatic pulses and using Dixon methods for water/fat separation. The spin-lock RF pulse sequence can be, for example, an adiabatic continuous-wave constant-amplitude spin-lock (ACCSL) pulse sequence. Data acquisition can use any acquisition method compatible with Dixon methods. Following data acquisition, a source image can be generated and analyzed (e.g., using Dixon methods) to generate separate water and fat images. A spatial distribution of a spin-lock based imaging biomarker (e.g., T1rho) can be determined from the water image and/or the fat image.

18 Claims, 12 Drawing Sheets

(56) References Cited

OTHER PUBLICATIONS

Yu, et al. "Multiecho reconstruction for simultaneous water-fat decomposition and T2* estimation." Journal of Magnetic Resonance Imaging 26, No. 4 (2007): 1153-1161.

Yu, et al. "Multiecho water-fat separation and simultaneous R estimation with multifrequency fat spectrum modeling." Magnetic Resonance in Medicine: An Official Journal of the International Society for Magnetic Resonance in Medicine 60, No. 5 (2008): 1122-1134.

* cited by examiner

SYSTEM AND METHOD FOR SEPARATION OF WATER AND FAT SIGNALS DURING SPIN-LOCK MAGNETIC RESONANCE IMAGING

BACKGROUND

This disclosure relates generally to magnetic resonance imaging (MRI) techniques, and in particular to techniques for separation of water and fat signals during spin-lock MRI. Such techniques can be used, for example, in T1rho imaging and quantification as well as other imaging biomarkers.

Magnetic resonance imaging (MRI) is a noninvasive diagnostic technique that can allow assessments of the composition and state of various tissues. In an MRI procedure, a patient is placed in a strong longitudinal magnetic field (B0) that aligns nuclear spins of atoms in the patient's body, producing a net magnetization vector. Radiofrequency (RF) pulses with magnetic field components (B1) transverse to the longitudinal field and frequencies tuned to the Larmor frequency of an isotope of interest (often $_1$H) are applied. These pulses can flip spins into a higher energy state, resulting in a transverse component to the magnetization vector. As these spins return to the ground state, responsive magnetic resonance signals from the patient's body can be detected. Based on these signals, characteristics of the magnetization can be measured.

Spin-lock techniques in MRI generally involve applying a long RF pulse (referred to as a "spin-lock" pulse) to lock the magnetization around an effective magnetic field. Such techniques can be used to quantify various imaging biomarkers that may reveal helpful information as to the macromolecular content of tissue. For instance, the spin-lattice relaxation time in the rotating frame (T1rho, or T1ρ) characterizes the decay (or relaxation) rate of spins during the spin-lock process. Because a number of diseases begin to alter the macromolecular content of tissue at a very early stage, spin-lock MRI offers the potential for early detection of disease. In addition, spin-lock MRI can potentially be used to monitor the effectiveness of treatment at the macromolecular level.

Conventional spin-lock MRI techniques are highly susceptible to the presence of fat, in part because protons in fat molecules have a chemical shift that can cause failure of spin-lock. For tissues that include infiltrative fatty tissue, this can result in artifacts and quantification errors. To reduce such artifacts and errors, spectrally selective RF pulses have been applied (e.g., prior to the spin-lock pulse) to suppress the fat signal. This approach is limited, however, in part because the approach is susceptible to B0 field inhomogeneity (which is common in modern MRI systems) and in part because fat has multiple chemical shift components, each with a different chemical shift, and a spectrally selective RF pulse cannot suppress all of these components.

Accordingly, improved techniques for fat suppression during spin-lock MRI would be desirable.

SUMMARY

Certain embodiments of the present invention relate to separation of fat and water signals in spin-lock MRI. In some embodiments, separation of fat and water signals can be achieved by a technique that includes using a spin-lock RF pulse sequence that incorporates adiabatic pulses and using Dixon methods for water/fat separation. The spin-lock RF pulse sequence can be, for example, an adiabatic continuous-wave constant-amplitude spin-lock (ACCSL) pulse sequence, which can include an adiabatic half passage (AHP), a constant-amplitude spin-lock RF pulse having a spin-lock time, and a reverse AHP, where the AHP and the reverse AHP have an RF amplitude equal to the spin-lock amplitude. Data acquisition can use any acquisition method compatible with Dixon methods. Following data acquisition, a source image can be generated (e.g., using conventional techniques for generating images from MRI data). The source image can be analyzed to generate separate water and fat images. In some embodiments, a spatial distribution of a spin-lock based imaging biomarker (e.g., T1rho) can be quantitatively determined, e.g., from the water image. To the extent that the water image is free of contributions from the fat signal, the reliability of quantification can be improved.

The following detailed description, together with the accompanying drawings, provides a further understanding of the nature and advantages of the claimed invention.

BRIEF DESCRIPTION OF THE DRAWINGS

FIGS. 6A-6F show examples of Bloch simulation results for fat peaks. FIGS. 6A-6C show results for parameters $g_n(TSL)$, $\varphi(TSL)$, $\beta_n(TSL)$, respectively, using a conventional spin-lock method, and FIGS. 6D-6F show results for parameters $g_n(TSL)$, $\varphi(TSL)$, and $\beta_n(TSL)$, respectively, using an ACCSL pulse sequence according to an embodiment of the present invention.

FIG. 5A shows amplitude coefficients $\beta_n(TSL)$ obtained using an ACCSL pulse sequence and Dixon methods according to an embodiment of the present invention, and FIG. 5B shows amplitude coefficients $\beta_n(TSL)$ obtained using a conventional spin-lock pulse and Dixon methods.

DETAILED DESCRIPTION

Figure 1:
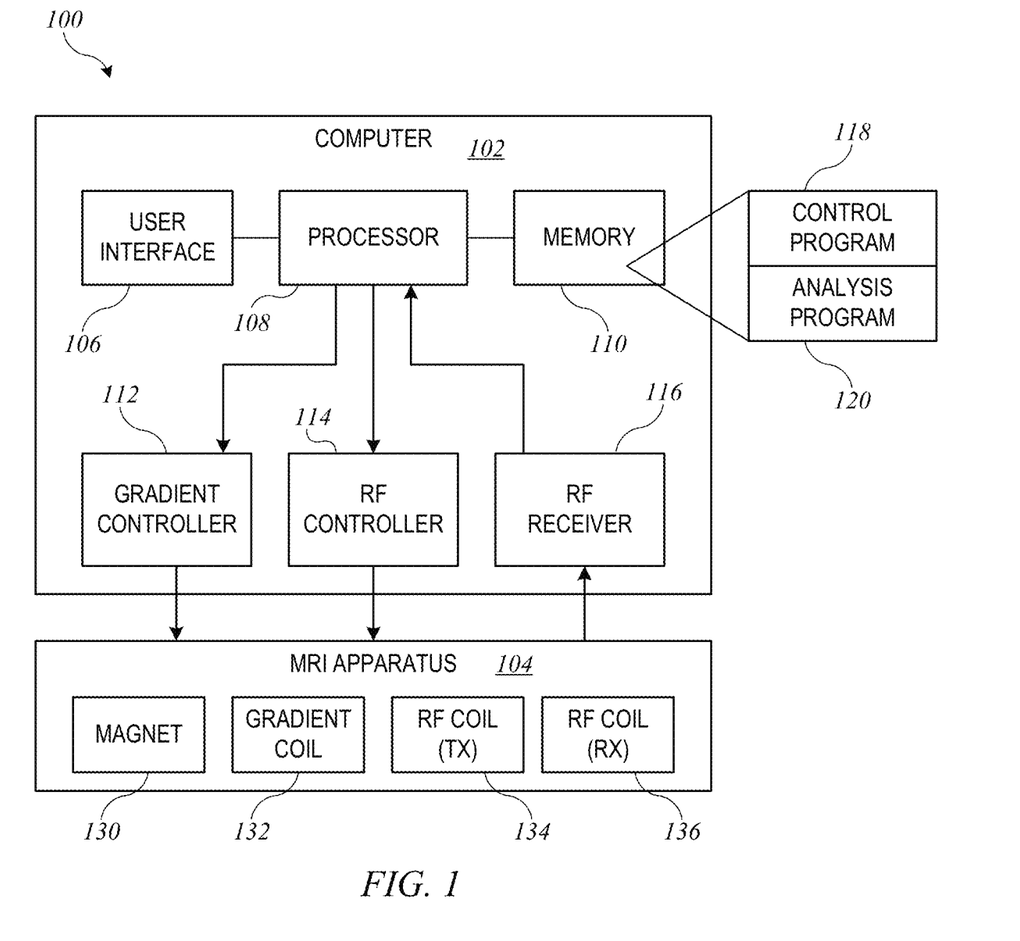
FIG. 1 shows an MRI system that can be used in connection with practicing some embodiments of the present invention.

FIG. 1 shows an MRI system that can be used in connection with practicing some embodiments of the present invention. MRI system 100 includes a computer 102 communicably coupled to an MRI apparatus 104.

Computer 102 can be of generally conventional design and can include a user interface 106, a processor 108, a memory 110, a gradient controller 112, an RF controller 114, and an RF receiver 116. User interface 106 can include components that allow a user (e.g., an operator of MRI system 100) to input instructions or data and to view information. For example, user interface 106 can include a keyboard, mouse, joystick, display screen, touch-sensitive display screen, and so on. Processor 108 can include a general purpose programmable processor (or any other processor or set of processors) capable of executing program code instructions to perform various operations. Memory 110 can include a combination of volatile and nonvolatile storage elements (e.g., DRAM, SRAM, flash memory, magnetic disk, optical disk, etc.). Portions of memory 110 can store program code to be executed by processor 108. Examples of the program code can include a control program 118, which can coordinate operations of MRI apparatus 104 as described below in order to acquire data, and an analysis program 120, which can perform analysis algorithms on data acquired from MRI apparatus 104. Gradient controller 112, RF controller 114, and RF receiver 116 can incorporate standard communication interfaces and protocols to communicate with components of MRI apparatus 104 as described below.

MRI apparatus 104 can be of generally conventional design and can incorporate a magnet 130, a gradient coil 132, and RF coils 134, 136. Magnet 130 can be a magnet capable of generating a large constant magnetic field B0 (e.g., 1.5 T, 3.0 T, or the like) in a longitudinal direction, in a region where a patient (or other subject to be imaged) can be placed. Gradient coil 132 can be capable of generating gradients in the constant magnetic field B0; operation of gradient coil 132 can be controlled by computer 102 via gradient controller 112. RF coils 134, 136 can include a transmitter (TX) coil 134 and a receiver (RX) coil 136. In some embodiments, a single coil can serve as both transmitter and receiver. In some embodiments, RF transmitter coil 134 can be placed around the portion of the subject's body that is to be imaged while RF receiver coil 136 is placed elsewhere within MRI apparatus 104. The preferred placement of RF coils 134, 136 may depend on the specific portion of the body that is to be imaged; those skilled in the art with access to the present disclosure will be able to make appropriate selections.

In operation, computer 100 can drive gradient coil 132 using gradient controller 112 to shape the magnetic field around the region being imaged. Computer 100 can drive RF transmitter coil 134 using RF controller 114 to generate RF pulses at a resonant frequency for an isotope of interest, driving nuclear spins into an excited state. RF receiver coil 136 can detect RF waves generated by the spins relaxing from the excited state when RF pulses are not being generated. RF receiver 116 can include amplifiers, digital-to-analog converters, and other circuitry to generate digital data from the RF waves detected by RF receiver coil 136. RF receiver 116 can provide this data to processor 108 for analysis.

MRI system 100 is illustrative, and many variations and modifications are possible. Those skilled in the art will be familiar with a variety of MRI apparatus and control systems and with basic principles of MRI data acquisition, including the use of gradient fields and RF pulses, as well as techniques for detecting signals responsive to RF pulses and processing those signals to generate images.

In some embodiments, MRI system 100 or other MRI apparatus can be used to generate pulse sequences suitable for spin-lock imaging of a subject, such as a specific organ or tissue within a patient. Examples of pulse sequences and imaging operations are described below.

Typical MRI imaging processes include a "preparation" phase and an "acquisition" phase. During the preparation phase, various pulse sequences can be generated in RF transmitter coil 134 to create a desired state of the magnetization vectors of nuclei of interest. For instance, a "reset" sequence may be used to reset net magnetization such that net magnetization becomes zero. Other types of preparation can include pulse sequences designed to suppress signals from specific types of tissue not of interest (e.g., blood, fat). For imaging techniques based on spin-lock, such as T1rho imaging, the preparation phase can include a magnetization prep sequence, which locks the magnetization around an effective magnetic field. The acquisition can be performed using various sequences such as fast spin echo sequences or other sequences as desired.

In embodiments described herein, a magnetization prep sequence for spin-lock imaging includes a spin-lock RF pulse of constant amplitude and frequency. During spin lock, spins follow a constant relaxation rate. By collecting relaxation-weighted images with different time of spin-lock (TSL), a relaxation parameter value can be measured by fitting the collected images to a relaxation model. While some examples herein use T1rho as the relaxation parameter, it is to be understood that similar techniques can be used for measuring other imaging biomarkers.

In certain embodiments of the present invention, separation of fat and water signals is accomplished through a technique that includes using a modified spin-lock RF pulse sequence that incorporates adiabatic pulses and using Dixon methods for water-fat separation.

Examples of spin-lock RF pulse sequences that incorporate adiabatic pulses have been previously described in W. Chen, "Artifacts correction for T1rho imaging with constant amplitude spin-lock," *J. Magnetic Resonance* 274:13-23 (2017); B. Jiang et al., "On-resonance and off-resonance continuous wave constant amplitude spin-lock and T1ρ quantification in the presence of B1 and B0 inhomogeneities," *NMR in Biomedicine* 25:e3928 (2018); and U.S. Patent Application Publication No. 2018/0031661 A1. As used herein, an adiabatic continuous-wave constant-amplitude spin-lock (ACCSL) pulse sequence is a spin-lock pulse sequence that includes an adiabatic half passage (AHP) prior to the spin-lock pulse and a reverse AHP following the spin-lock pulse.

Figure 2A:
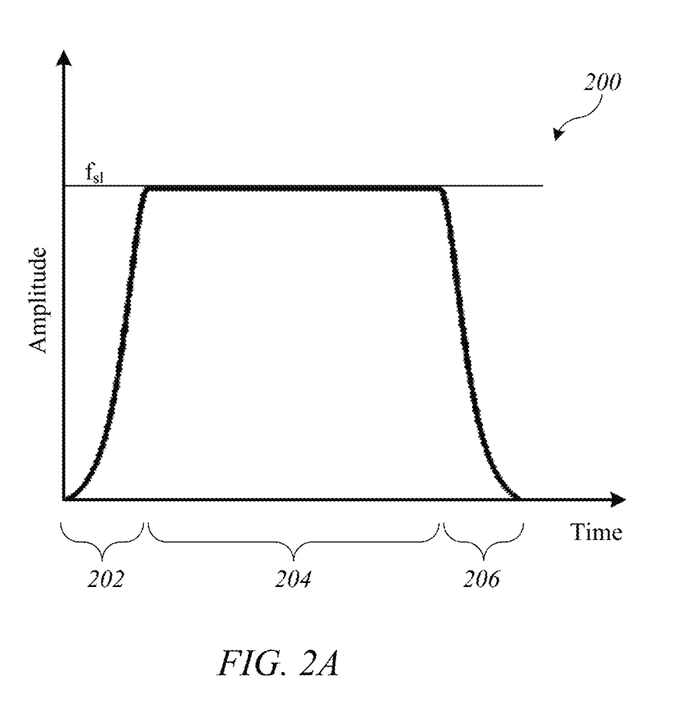
FIGS. 2A-2C show schematic diagrams of characteristics of an ACCSL pulse sequence that can be used in some embodiments of the present invention.
Figure 2B:
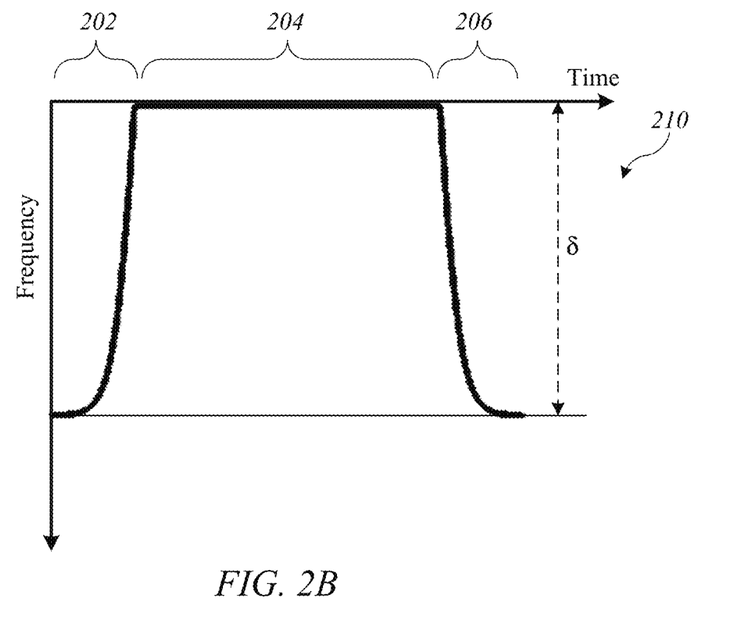
Figure 2C:
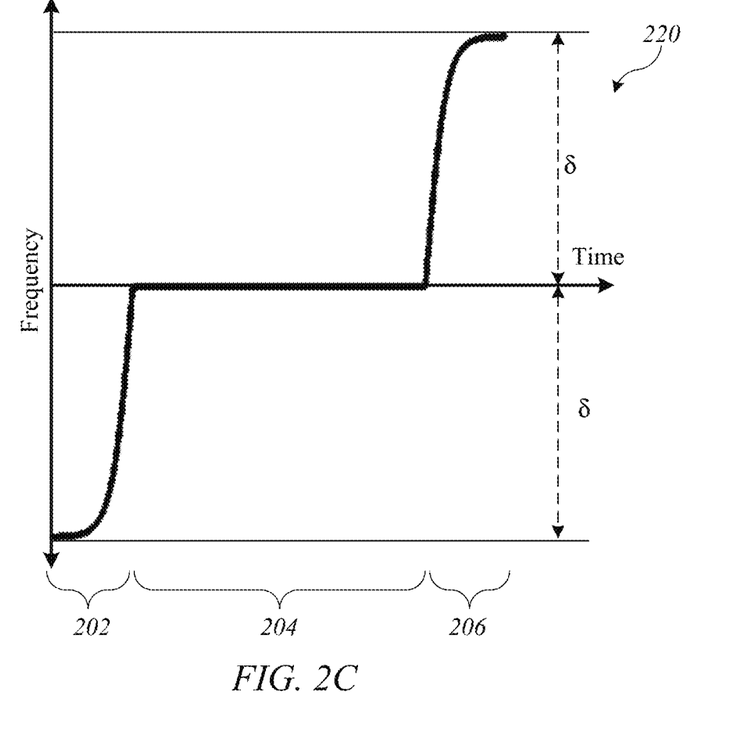

FIGS. 2A-2C show schematic diagrams of characteristics of RF pulse clusters that can be used in an ACCSL pulse sequence in some embodiments of the present invention. FIG. 2A shows an amplitude modulation waveform 200; FIGS. 2B and 2C show frequency modulation waveforms 210 and 220. It is to be understood that amplitude modulation waveform 200 can be used with either frequency modulation waveform 210 or frequency modulation waveform 220. Waveforms 200, 210, 220 each include an AHP (segment 202), a spin-lock pulse of duration TSL (segment 204), and a reverse AHP (segment 206). In some embodiments, AHP segment 202 can be an HS1 or "stretched" HSn pulse based on a hyperbolic secant function, e.g., as described in Silver et al., "Highly selective π/2 and π pulse generation," *J. Magn. Reson.* 59:347-531 (1984). Reverse AHP segment 206 can be a time-reversed version of AHP segment 202. Other functions can be substituted.

Figure 3A:
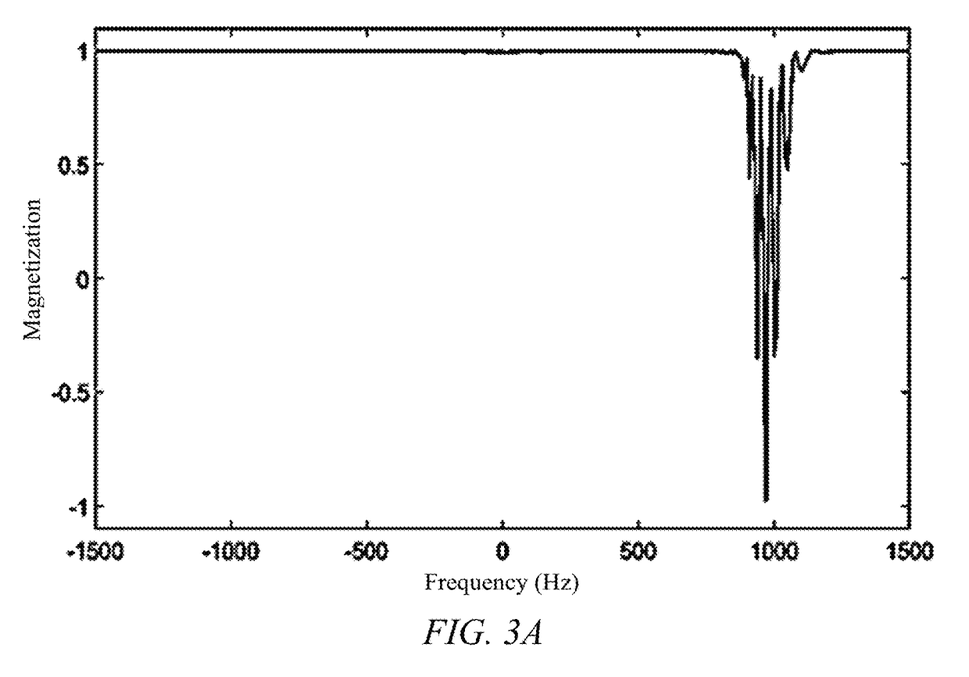
FIG. 3A shows the frequency spectrum of an ACCSL RF pulse cluster with the amplitude waveform of FIG. 2A and the frequency waveform of FIG. 2B.
Figure 3B:
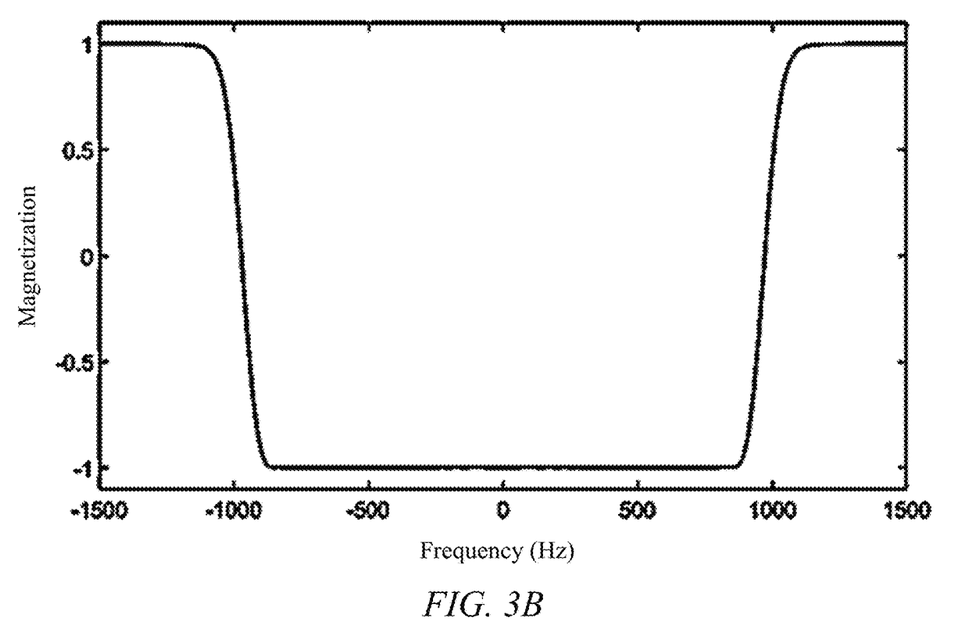
FIG. 3B shows the frequency spectrum of an ACCSL RF pulse cluster with the amplitude waveform of FIG. 2A and the frequency waveform of FIG. 2C.
Figure 4A:
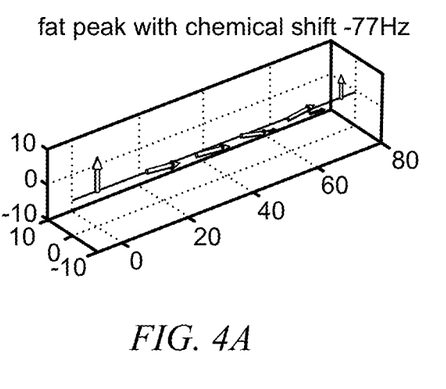
FIGS. 4A-4L are time plots showing simulated magnetization evolution for fat peaks during spin-lock for conventional methods using hard RF spin-lock pulses (FIGS. 4A-4F) and for a method using an ACCSL pulse sequence according to an embodiment of the present invention (FIGS. 4G-4L).
Figure 4B:
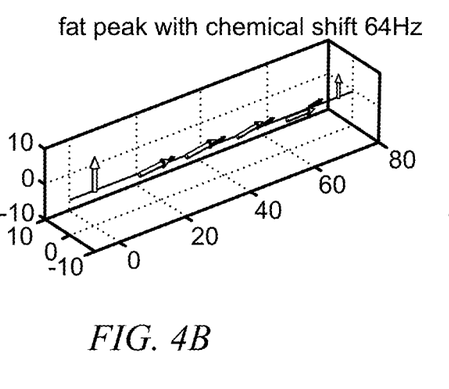
Figure 4C:
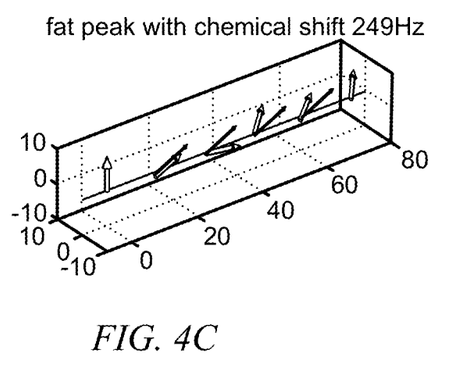
Figure 4D:
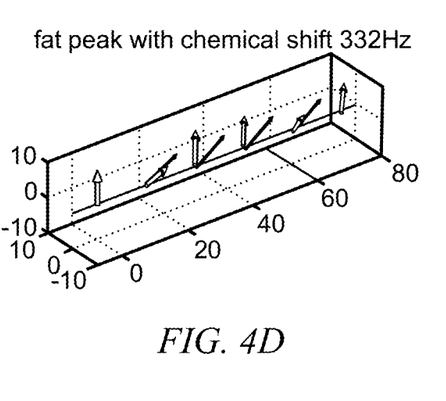
Figure 4E:
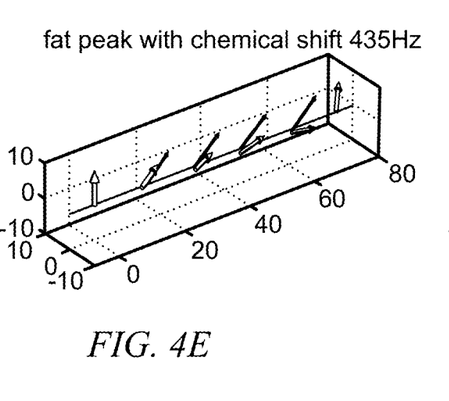
Figure 4F:
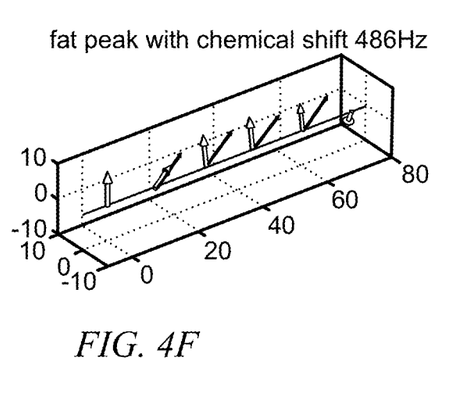
Figure 4G:
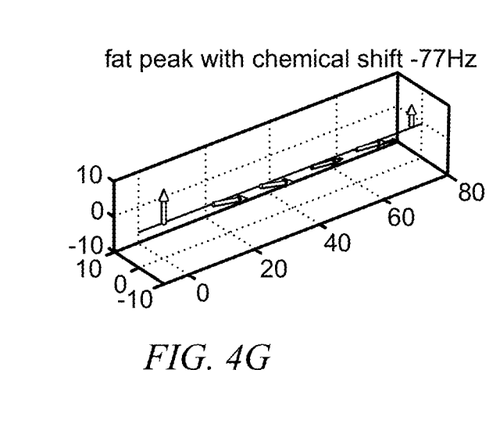
Figure 4H:
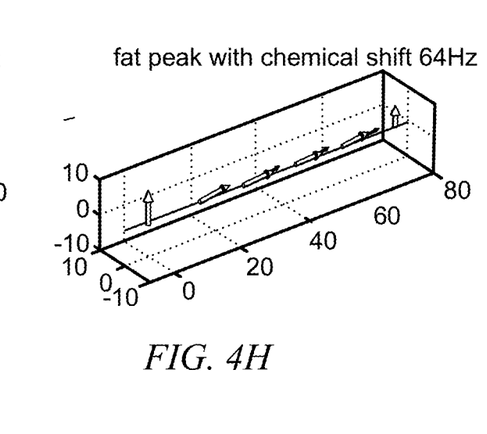
Figure 4I:
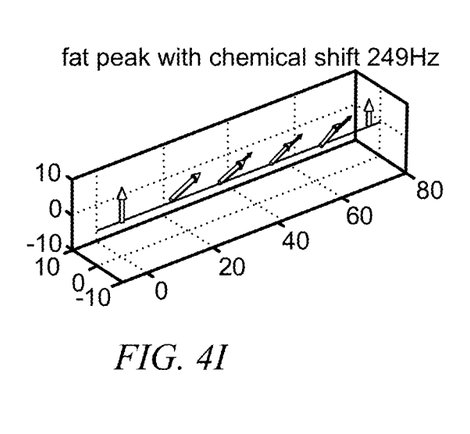
Figure 4J:
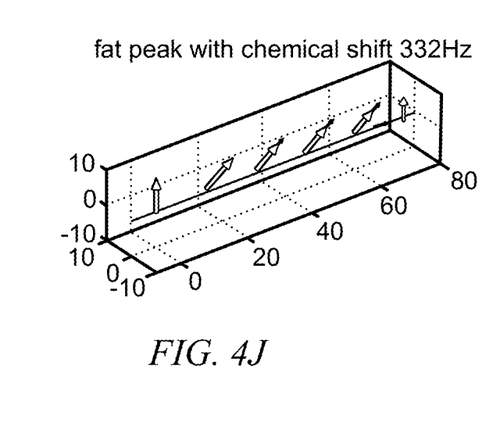
Figure 4K:
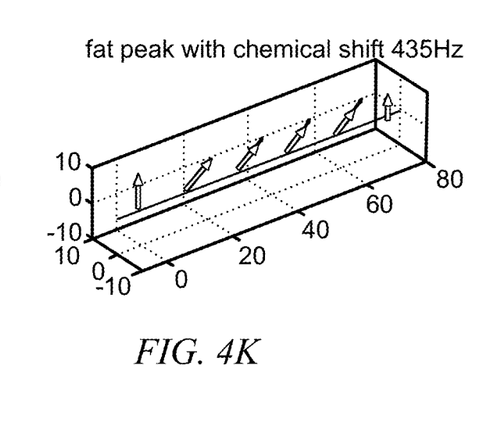
Figure 4L:
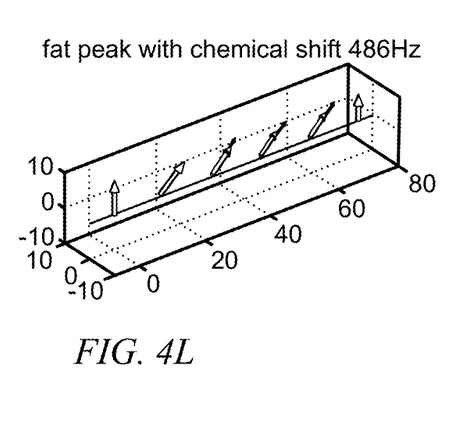

FIGS. 3A and 3B shows the frequency spectrum of the ACCSL RF pulse clusters shown in FIGS. 2A-2C. Specifically, FIG. 3A shows the frequency spectrum of an ACCSL RF pulse cluster with the amplitude waveform of FIG. 2A and the frequency waveform of FIG. 2B, while FIG. 3B shows the frequency spectrum of an ACCSL RF pulse cluster with the amplitude waveform of FIG. 2A and the frequency waveform of FIG. 2C. In some embodiments, the fat peaks are placed within the passband of the RF pulse cluster, and the frequency modulation waveform of the ACCSL RF pulses is designed to meet this condition.

According to some embodiments of the present invention, ACCSL pulse sequences of the kind shown in FIGS. 2A-2C can be used to provide simultaneous spin-lock of water and fat spins at multiple spectral peaks. FIGS. 4A-4L are time plots showing simulated magnetization evolution for fat peaks during spin-lock for conventional methods (using hard RF pulses) and for a method using an ACCSL pulse sequence according to an embodiment of the present invention. To generate these time plots, a Bloch simulation was performed using six spectral fat peaks at chemical shifts of −3.80, −3.40, −2.60, −1.94, −0.39, and 0.60 ppm. The time plots shown in FIGS. 4A-4F were generated using a conventional spin-lock RF pulse cluster and show time evolution of the magnetization spin (thick arrows) and effective spin-lock field (thin arrows) for fat components with six different chemical shifts. As can be seen, spin lock is not achieved at any of the chemical shifts. In practice, this can be expected to result in image artifacts. In contrast, the time plots shown in FIGS. 4G-4L were generating using an ACCSL pulse sequence and show time evolution of the magnetization spin (thick arrows) and effective spin-lock field (thin arrows) for fat components with the same six chemical shifts as FIGS. 4A-4F. As can be seen, when an ACCSL pulse sequence is used, spin-lock can be achieved simultaneously for all fat spins across a wide spectral bandwidth.

Dixon methods for water/fat separation are well-known. As described in W. T. Dixon, "Simple proton spectroscopic imaging," *Radiology* 153:189-194 (1984), water and fat molecules precess at different frequencies. Accordingly, they are in phase at some times and out of phase at others. By acquiring spin echo (or gradient echo) images with two (or more) different echo times (TE), it is possible to obtain "in-phase" and "out-of-phase" images. By combining these images appropriately, separate images for water and fat can be produced. The term "Dixon methods" is used herein to refer generally to image acquisition and analysis techniques that use the differential precession frequencies of water and fat molecules to generate separate water and fat images in a single imaging operation. The term "Dixon acquisition methods" is used herein to refer to the process of acquiring images with an appropriate set of echo times, and the term "Dixon analysis methods" is used herein to refer to analytic techniques for generating separate water and fat images from images acquired using Dixon acquisition methods.

Figure 5:
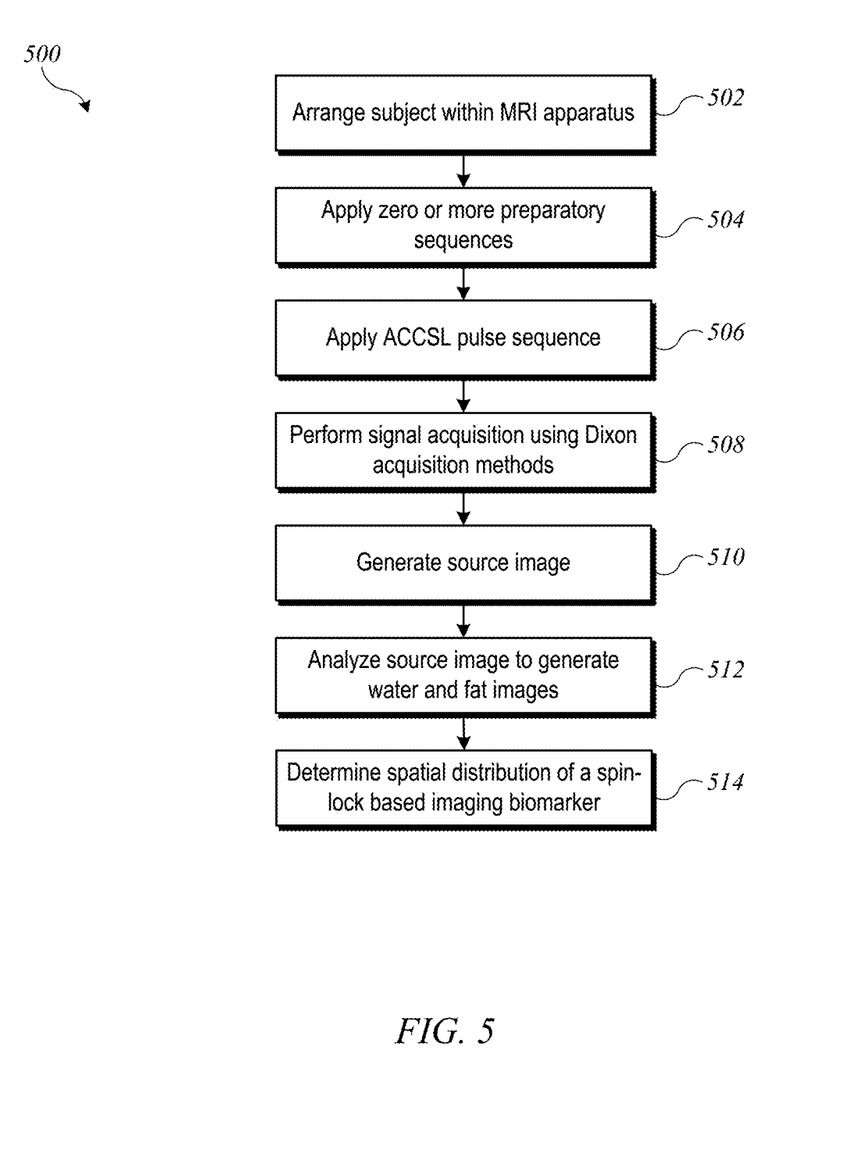
FIG. 5 shows a flow diagram of an MRI image acquisition process for spin-lock imaging according to an embodiment of the present invention.

According to some embodiments of the present invention, Dixon methods can be applied following an ACCSL pulse sequence to provide separation of water and fat signals. FIG. 5 shows a flow diagram of an MRI image acquisition process 500 for spin-lock imaging according to an embodiment of the present invention. Process 500 can be performed using an MRI apparatus such as MRI apparatus 100 of FIG. 1. At block 502, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 504, various preparatory pulse sequences can be applied. Examples include magnetization reset sequences, suppression sequences to reduce the effect of selected tissue types (e.g., blood, etc.), and the like. Such sequences can be conventional and are optional; a detailed description is omitted as not being critical to understanding the claimed invention.

At block 506, an ACCSL pulse sequence is applied. For example, the ACCSL pulse sequence can have amplitude and frequency modulation characteristics as described above with reference to FIGS. 2A and 2B, or with reference to FIGS. 2A and 2C.

At block 508, signal acquisition can be performed using Dixon acquisition methods. Signal acquisition can include generating RF pulses to produce a signal from the subject and operating an RF receiver coil to detect the signal. Various acquisition sequences can be performed, including fast spin echo (FSE) sequences. In accordance with Dixon acquisition methods, multi-shot FSE sequences using sets of echo times (the difference in echo times between acquisitions within a set is denoted herein as Δ(TE)) can be used to enable extraction of in-phase and out-of-phase images. For example, a 3-point Dixon acquisition method can be used with Δ(TE)=0 ms, 1 ms, and 2 ms. More generally, signal acquisition can use any technique that is compatible with Dixon methods for separation of water and fat images. During the signal acquisition, a data set can be collected.

At block 510, image data (also referred to as a "source" image) can be generated based on the data set collected during the signal acquisition. Conventional techniques for generating the image data can be applied; examples include Fourier transform of acquired k-space data.

At block 512, the source image can be analyzed to separate water and fat contributions, thereby generating a water image and a fat image. For example, after spin-lock preparation with a given TSL, a source image element s acquired at an echo time TE at location r can be expressed as:

$$s(r, TE, TSL) = \left(\rho_w(r, TSL) + \rho_f(r, TSL)\sum_{n=1}^{N_p} [\beta_n(TSL) \cdot e^{j2\pi f_n TE}]\right) \cdot e^{j2\pi \Psi(r) TE}, \quad (1)$$

where $\rho_w(r, TSL)$ and $\rho_f(r, TSL)$ are water and fat images, respectively; $\Psi(r)$ is the field map; $N_p$ is the total number of fat peaks; $f_n$ is the chemical shift of the nth fat peak; and $\beta_n(TSL)$ is the relative amplitude of the nth fat peak, normalized such that $$\sum_{n=1}^{N_p} \beta_n(TSL) = 1.$$

Assuming that the value of $\beta_n(TSL)$ for each fat peak can be determined, separate water images and fat images can be generated, e.g., by applying Dixon analysis methods to source images acquired with different Δ(TE) and using Eq. (1) to characterize the source image signal.

Use of an ACCSL pulse sequence can make it possible to reliably determine the value of $\beta_n(TSL)$ for each fat peak. The relative amplitude of each fat peak depends on TSL due to the difference in magnetization evolution of each individual fat peaks during spin-lock. For instance, if $\alpha_n$ is the amplitude coefficient of the nth fat peak in the absence of spin-lock preparation (these coefficients have been measured and documented in the literature), the amplitude coefficients after spin-lock with duration TSL can be expressed as:

$$\beta_n(TSL) = \alpha_n \cdot \frac{g_n(TSL)}{\varphi(TSL)}. \tag{2}$$

where $$\varphi(TSL) \triangleq \sum_{n=1}^{N_p} [\alpha_n \cdot g_n(TSL)]$$

so that $$\sum_{n=1}^{N_p} \beta_n(TSL) = 1.$$

The function $g_n(TSL)$ is used to characterize the magnetization evolution of the nth fat peak during the spin-lock RF pulse cluster.

For conventional spin-lock methods, fat spins cannot be locked during the spin-lock process due to the chemical shift effect. In the presence of spatially varying B1 RF and B0 field inhomogeneity, the magnetization evolution of fat spins during spin-lock is highly complicated, which makes it challenging to compute $g_n(TSL)$ and to perform water-fat separation with a multi-peak fat spectrum.

In contrast, where an ACCSL pulse sequence is used, the fat spins are well locked along the effective spin-lock field direction. This allows magnetization evolution corresponding to each fat peak to be characterized by a predefined simple T1rho relaxation model, as described in B. Jiang et al., "On-resonance and off-resonance continuous wave constant amplitude spin-lock and T1ρ quantification in the presence of B1 and B0 inhomogeneities," *NMR in Biomedicine* 25:e3928 (2018).

Figure 6A:
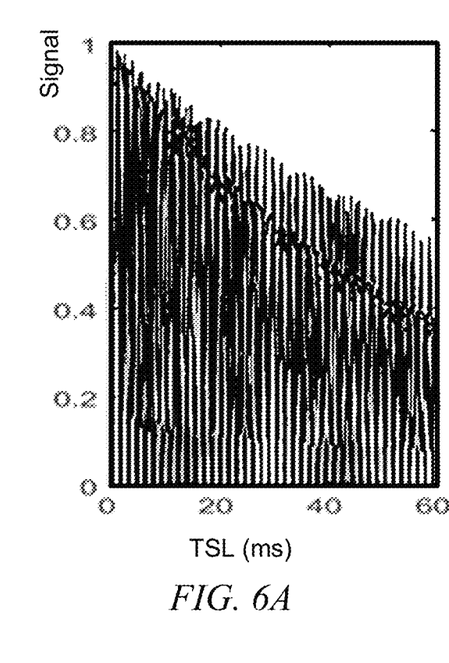
Figure 6B:
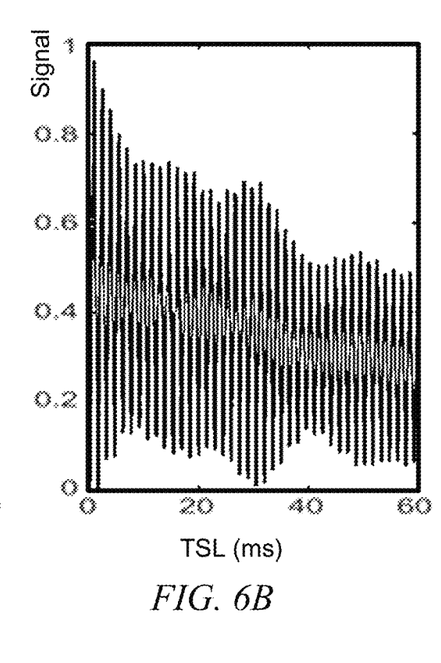
Figure 6C:
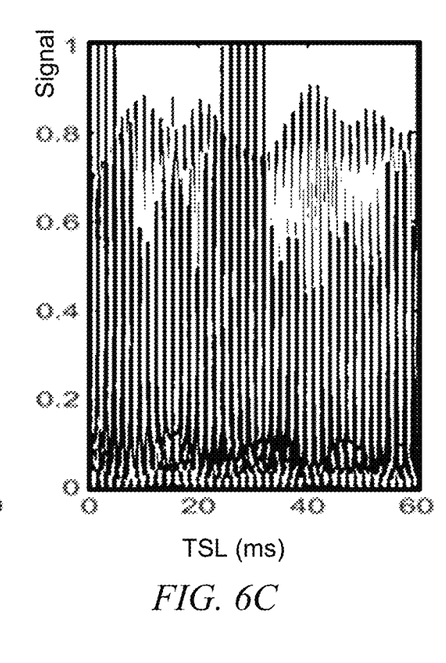
Figure 6D:
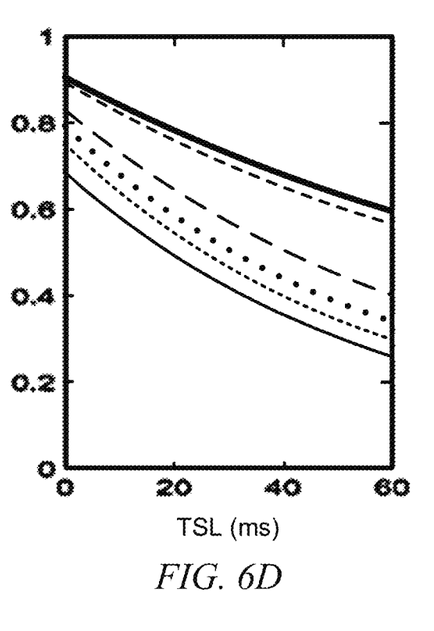
Figure 6E:
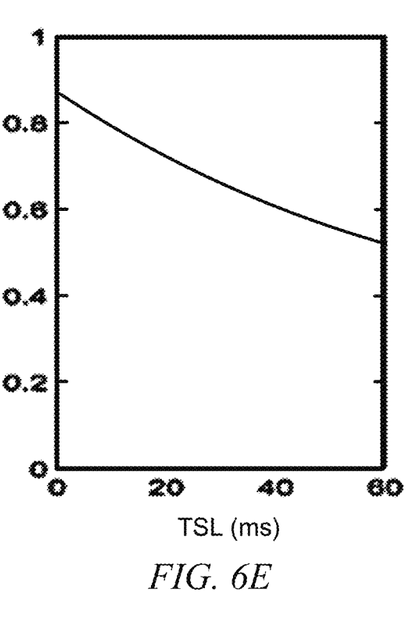
Figure 6F:
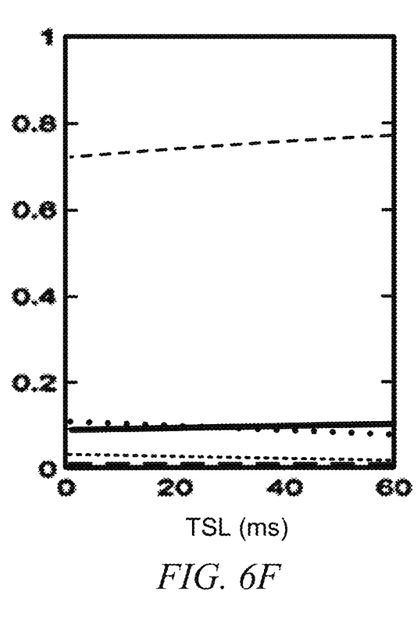

FIGS. 6A-6C show examples of Bloch simulation results for $g_n(TSL)$ (FIG. 6A), $\varphi(TSL)$ (FIG. 6B), and $\beta_n(TSL)$ (FIG. 6C) using a conventional spin-lock method. FIGS. 6D-6F show examples of Bloch simulation results for $g_n(TSL)$ (FIG. 6D), $\varphi(TSL)$ (FIG. 6E), and $\beta_n(TSL)$ (FIG. 6F) using an ACCSL pulse sequence. For the conventional spin-lock simulation (FIGS. 6A-6C), the failure of spin-lock for the fat spins results in significant oscillation of the magnetization evolution during the spin-lock, which results in unpredictable amplitude coefficients $\beta_n(TSL)$ for water-fat separation. For spin-lock using an ACCSL pulse sequence, the magnetization of fat peaks follows a regular exponential relaxation, which is characterized by $g_n(TSL)$. It should be noted that after normalization of $g_n(TSL)$ by $\varphi(TSL)$, the relaxation effect during TSL is mostly removed from the amplitude coefficient $\beta_n(TSL)$, and it can be conveniently approximated by the TSL-independent coefficient $\alpha_n$ (which, as noted above, is well measured). This effect is in part because fat has relatively long T2 and therefore relatively long T1rho. Further, ACCSL can be viewed as an off-resonance spin-lock at an effective angle that deviates from the transverse plane, which results in further prolonging T1rho of fat. The slow signal decay during TSL makes it possible to remove the bulk relaxation part of each fat peak by normalization with a single relaxation term.

Figure 7A:
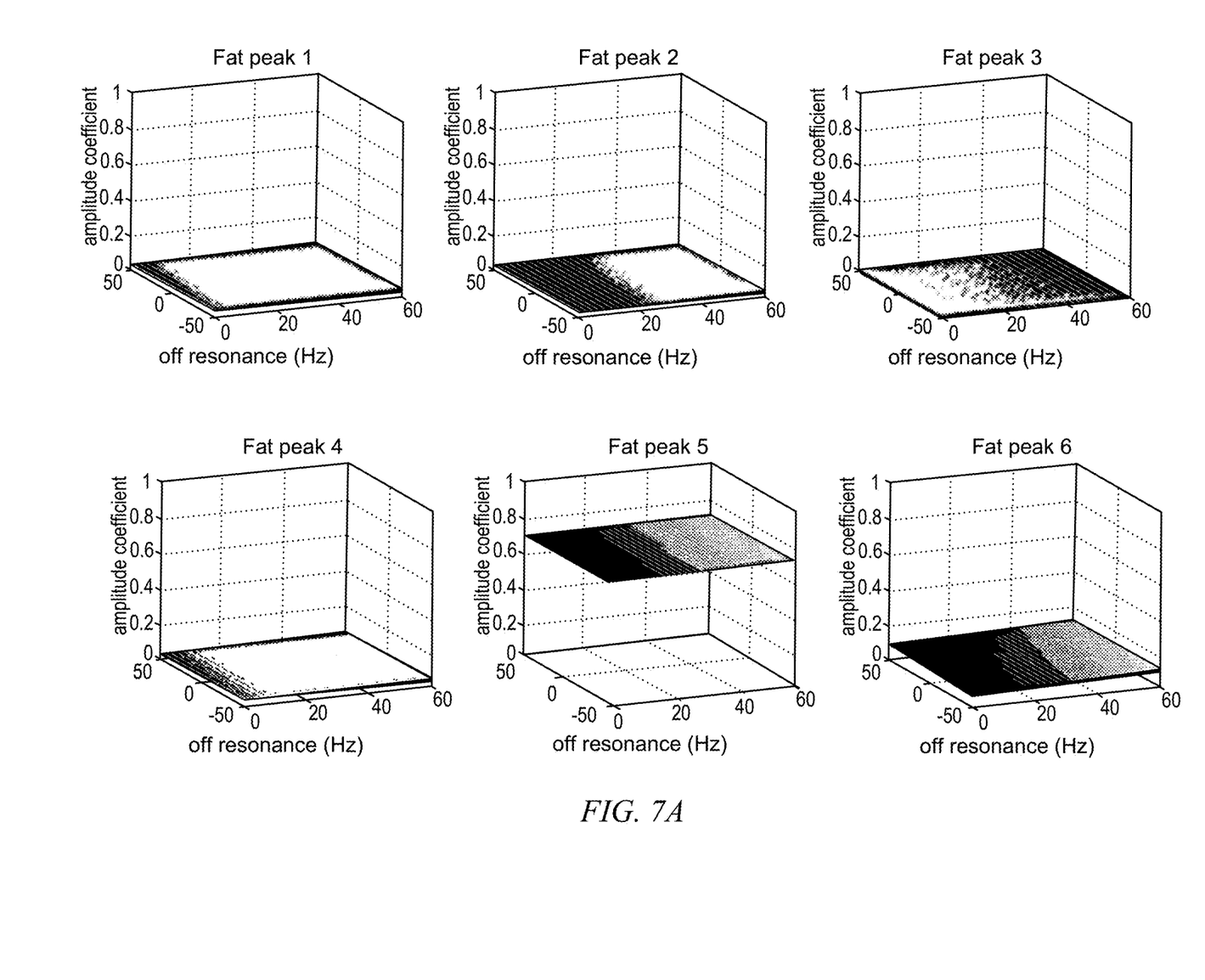
FIGS. 7A and 7B show results of full Bloch simulations of six amplitude coefficients.
Figure 7B:
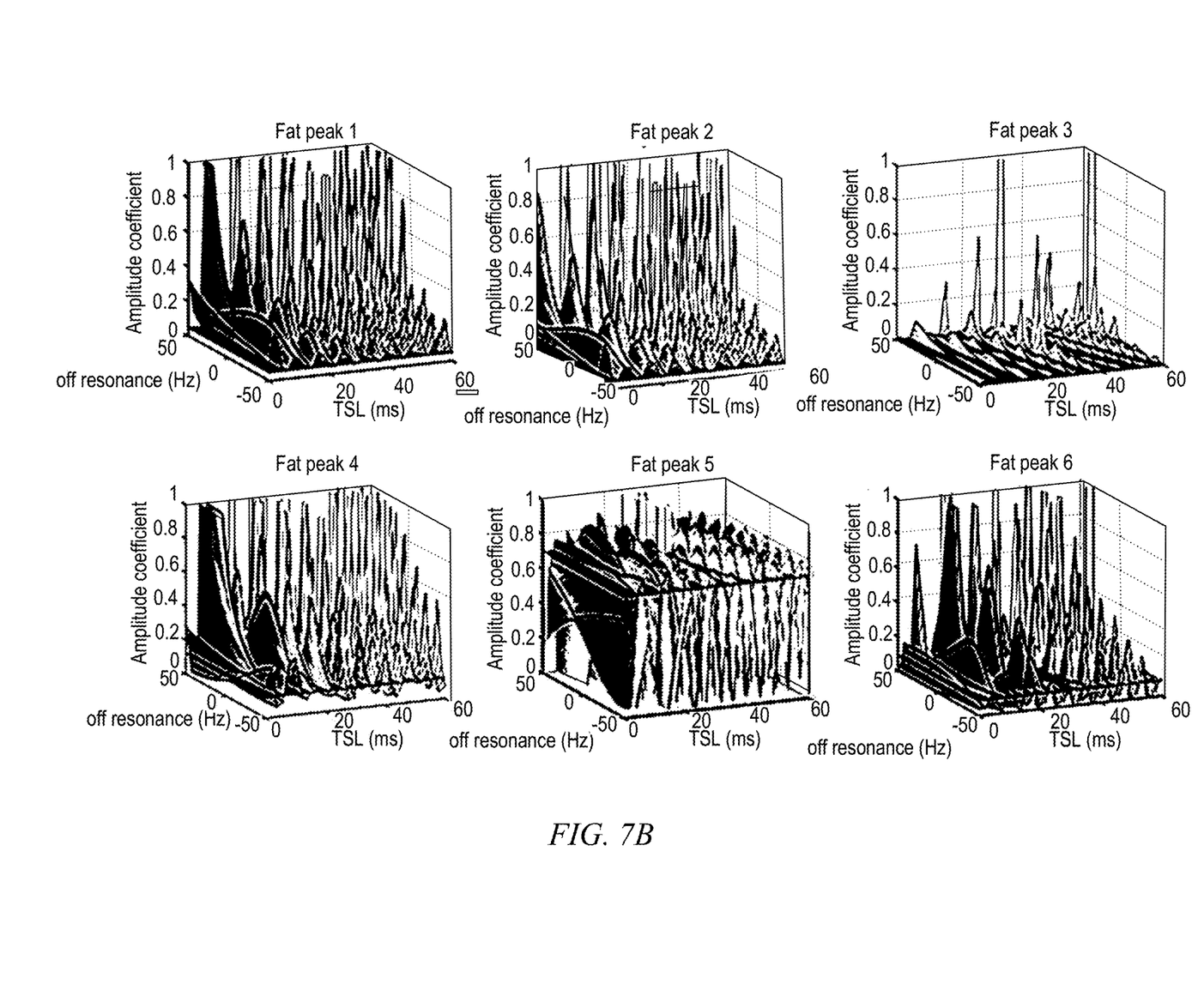

Further illustrating this effect, FIGS. 7A and 7B show results of full Bloch simulations of six amplitude coefficients $\beta_n(TSL)$ (corresponding to chemical shifts of −3.80, −3.40, −2.60, −1.94, −0.39, and 0.60 ppm), with the amplitude coefficients calculated based on simulation at different TSLs and different off-resonance frequencies. FIG. 7A shows plots of amplitude coefficients $\beta_n(TSL)$ obtained using an ACCSL pulse sequence and Dixon methods as described herein, and FIG. 7B shows amplitude coefficients $\beta_n(TSL)$ obtained using a conventional spin-lock pulse sequence and Dixon methods. As can be seen in FIG. 7B, the conventional spin-lock pulse results in significant oscillation of the amplitude coefficients, due to the susceptibility to chemical shift and B0 field inhomogeneity. Use of an ACCSL pulse sequence effectively eliminates the oscillation.

Consistently with the results in FIGS. 6D-6F, when an ACCSL pulse sequence is used, the amplitude coefficients $\beta_n(TSL)$ (after normalization) have little remaining dependence on TSL. (This effect can be seen in FIG. 7A.) Accordingly, in some embodiments, a first-order approximation to Eq. (1) can be substituted using TSL-independent amplitude coefficients to perform water-fat separation. In instances where this approximation results in significant error, a pre-calibration procedure can be performed to obtain the TSL-dependent amplitude coefficients $\beta_n(TSL)$. Examples of suitable pre-calibration procedures are known in the art and include pre-calibration procedures described in H. Yu et al., "Multiecho water-fat separation and simultaneous R2* estimation with multifrequency fat spectrum modeling," *Magnetic Resonance in Medicine* 60(5):1122-34 (2008) or in D. Weidlich et al., "In-vivo water T2 mapping in tissues containing water and fat using a T2-prepared 3D Dixon TSE sequence and a pre-calibrated fat spectrum model," *ISMRM 27th Annual Meeting*, 2018 *Paris, France* 4223 (2018).

It should be understood that Eq. (1) can be modified. For instance, in some embodiments, T2* decay can be included in the model of Eq. (1), e.g., using the method described in H. Yu et al., "Multiecho reconstruction for simultaneous water-fat decomposition and T2* estimation," *J. Magnetic Resonance Imaging* 26(4):1153-61 (2007). Other modifications are also possible.

Referring again to FIG. 5, at block 514, a spatial distribution of a spin-lock based imaging biomarker can be determined from the image data, including any combination of the source image, the water image, and/or the fat image. For example, T1rho can be determined by applying a relaxation model to the water image (or to the source image if desired). In some embodiments, a conventional monoexponential relaxation model can be used. Other relaxation models, such as a relaxation model as described in B. Jiang et al., "On-resonance and off-resonance continuous wave constant amplitude spin-lock and T1ρ quantification in the presence of B1 and B0 inhomogeneities," *NMR in Biomedicine* 25:e3928 (2018), can also be used. In some embodiments, spatial distributions can be computed for other spin-lock based imaging biomarkers, and embodiments of the invention are not limited to T1rho quantification.

Figure 8:
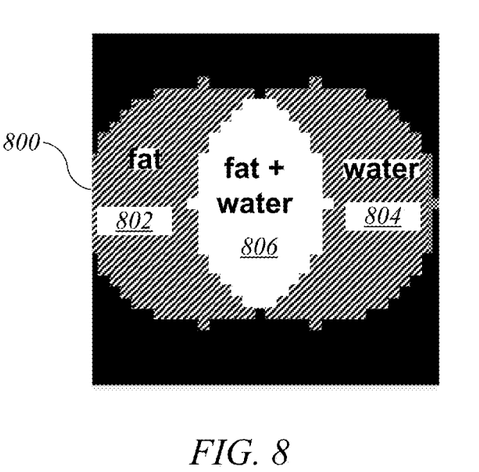
FIG. 8 illustrates a simulated phantom object incorporating fat and water.

To illustrate various benefits of the techniques described herein, simulation studies were conducted using the full equation Bloch simulation. For purposes of simulation, a numerical phantom object 800 incorporating fat and water was defined as shown in FIG. 8. Numerical phantom object 800 includes a fat region 802, a water region 804, and a fat+water "overlap" region 806 (simulating infiltrative fatty tissue). Simulated images were generated using four TSL values (0, 10, 20, and 50 ms), a spin-lock frequency of 500 Hz, and 3-point Dixon acquisition with Δ(TE) of 0, 1, and 2 ms. A smooth spatially-varying field map with off-resonance within a range from −50 Hz to +50 Hz was used in the simulation. Dixon analysis was performed using a method described in H. Yu et al., "Multiecho water-fat separation and simultaneous R2* estimation with multifrequency fat spectrum modeling," *Magnetic Resonance in Medicine* 60(5):1122-34 (2008). The simulation was performed for an ACCSL pulse sequence with Dixon methods as described herein (e.g., process 500) and for a conventional spin-lock pulse with Dixon methods. In each instance, a relaxation model described in B. Jiang et al., "On-resonance and off-resonance continuous wave constant amplitude spin-lock and T1ρ quantification in the presence of B1 and B0 inhomogeneities," *NMR in Biomedicine* 25:e3928 (2018) and a conventional mono-exponential relaxation model were used for T1rho quantification.

Figure 9A:
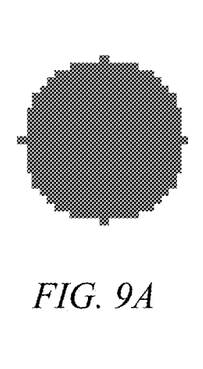
FIGS. 9A-9E show example T1rho maps computed from simulated images obtained using various techniques. Shown are: ground truth (FIG. 9A); a map obtained from a simulated source image (FIG. 9B); a map obtained using a simulation of a conventional spin-lock pulse with Dixon method (FIG. 9C); and maps obtained using simulation of an ACCSL pulse sequence with Dixon method according to an embodiment of the present invention (FIGS. 9D and 9E).
Figure 9B:
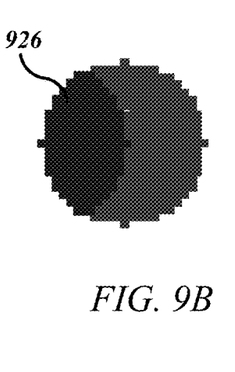
Figure 9C:
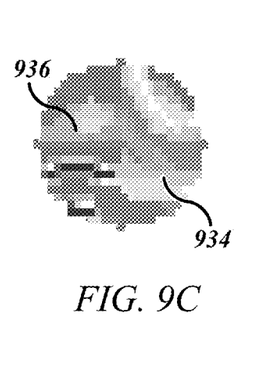
Figure 9D:
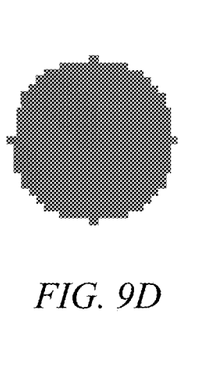
Figure 9E:
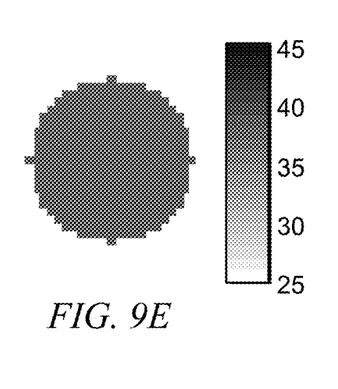

FIGS. 9A-9E show example T1rho maps of water tissue obtained from the simulations. The maps are color-coded to the scale shown at the right of FIG. 9E. FIG. 9A shows a ground truth T1rho map for a region of interest (ROI) corresponding to the union of water region 804 and fat+water region 806 in phantom object 800. (Fat region 802 is ignored.) FIG. 9B shows a T1rho map of the same ROI obtained from source images (i.e., with no fat suppression). The T1rho values are significantly higher than ground truth, and fat contributes in the region 926 corresponding to region 806. FIG. 9C shows a T1rho map obtained from water images generated using a conventional spin-lock RF pulse cluster with Dixon methods. The T1rho values are closer to ground truth, but artifacts (banding) can be seen. The banding artifacts in region 934 (corresponding to region 804) are due to B0 field inhomogeneity effects, and the banding artifacts in region 936 (corresponding to region 806) are due to the combined effect of B0 field inhomogeneity and the chemical shift of fat components. FIG. 9D shows a T1rho map obtained from water images generated using an ACCSL pulse sequence with Dixon methods (e.g., process 500) without pre-calibration of amplitude coefficients $\beta_n(TSL)$. The T1rho values are close to ground truth and artifacts are not visible. FIG. 9E shows a T1rho map obtained from water images generated using an ACCSL pulse sequence with Dixon methods (e.g., process 500) with pre-calibration of amplitude coefficients $\beta_n(TSL)$. The T1rho values in FIG. 9E are even closer to ground truth than in FIG. 9D.

Figure 10:
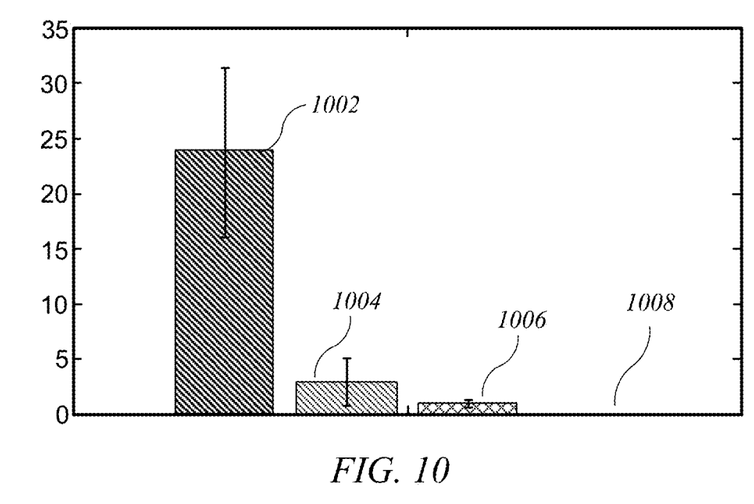
FIG. 10 shows a bar graph summarizing the percentage error in T1rho quantification for the images of FIGS. 9B-9E.

FIG. 10 shows a bar graph summarizing the percentage error in T1rho quantification for the images of FIGS. 9B-9E. Bar 1002 corresponds to the image of FIG. 9B (no fat suppression); bar 1004 to the image of FIG. 9C (conventional spin-lock pulse with Dixon methods); bar 1006 to the image of FIG. 9D (ACCSL pulse sequence with Dixon methods, without precalibration of amplitude coefficients $\beta_n(TSL)$); and bar 1008 to the image of FIG. 9E (ACCSL pulse sequence with Dixon methods, with precalibration of amplitude coefficients $\beta_n(TSL)$). (Error percentage in the last case is low enough not to be visible.) As can be seen, use of a conventional spin-lock RF pulse cluster with Dixon methods for fat/water separation can provide significant reduction of fat signal in water images, while the use of an ACCSL pulse sequence with Dixon methods provides even greater reduction of fat signal in water images. Pre-calibration of amplitude coefficients $\beta_n(TSL)$ may allow the T1rho quantification error to be reduced to nearly zero.

These examples illustrate that methods and systems described herein, in which spin-lock MRI data acquisition incorporates an ACCSL pulse sequence in combination with Dixon methods for water/fat separation, can provide significant improvement in the ability to provide accurate and robust spin-lock MRI images in the presence of fat.

While the invention has been described with reference to specific embodiments, those skilled in the art will appreciate that numerous modifications are possible. For example, the pulse sequence parameters described above can be modified, and additional pulse sequences can be incorporated as desired. Other modulation waveforms can be applied to define the AHP and/or reverse AHP in the ACCSL pulse sequence.

It should also be understood that although the present description makes specific reference to T1rho as a parameter of interest, T1rho is not the only parameter that is studied using spin-lock RF pulses. Accordingly, techniques described herein are not limited to T1rho imaging; they can also be applied in other imaging technologies based on spin-lock.

The analysis techniques described herein can be implemented using computer programs that may be executable on a variety of general-purpose or special-purpose computing devices, and those skilled in the art with access to the present disclosure will be capable of writing appropriate program code. The output of the computer programs may include numerical values (e.g., in list or tabular form), images (e.g., renderings generated using the image data), graphical output (e.g., images or graphs), and may be provided on a display, on a paper printout, in an electronic document that can be transmitted via electronic communication channels (e.g., email, secure FTP server, or the like), or in any other format that can be perceived and interpreted by a clinician. It should be noted that the data analysis can be but need not be performed by the MRI system used to acquire the MRI data. In some embodiments, the MRI system can be used to collect image data that is transferred to a separate computer system for analysis. Computer programs may be stored in any type of computer-readable storage medium (e.g., optical, magnetic, semiconductor-based or other non-transitory storage media) and may also be distributed using transitory computer-readable media (e.g., Internet download).

Thus, although the invention has been described with respect to specific embodiments, it will be appreciated that the invention is intended to cover all modifications and equivalents within the scope of the following claims.

What is claimed is:

1. A method of generating an image of a region of interest of a subject using a magnetic resonance imaging (MRI) apparatus, the method comprising:
    applying a magnetization prep sequence that includes an adiabatic continuous-wave constant-amplitude spin-lock (ACCSL) pulse sequence;
    performing an acquisition sequence to acquire a data set wherein the acquisition sequence incorporates a Dixon acquisition method;
    generating a source image from the data set; and analyzing the source image using a Dixon analysis method to generate a water image and a fat image.

2. The method of claim 1 further comprising:
determining, based on at least the water image, a spatial distribution of a spin-lock based imaging biomarker for each of a plurality of locations within the region of interest.

3. The method of claim 2 wherein the spin-lock based imaging biomarker is T1rho.

4. The method of claim 1 wherein the ACCSL pulse sequence includes an adiabatic half passage (AHP), a constant-amplitude spin-lock radiofrequency (RF) pulse having a spin-lock time, and a reverse AHP, wherein an RF amplitude of the AHP and the reverse AHP is equal to a spin-lock amplitude.

5. The method of claim 1 wherein the Dixon acquisition method is a 3-point Dixon method.

6. The method of claim 1 wherein analyzing the data set to generate a water image and a fat image includes modeling the source image as:

$$s(r, TE, TSL) = \left(\rho_w(r, TSL) + \rho_f(r, TSL) \sum_{n=1}^{N_p} [\beta_n(TSL) \cdot e^{j2\pi f_n TE}]\right) \cdot e^{j2\pi \Psi(r) TE},$$

wherein $s(r, TE, TSL)$ is a source image element acquired at a location r with spin-lock time TSL and echo time TE; $\rho_w(r, TSL)$ and $\rho_f(r, TSL)$ are the water and fat images, respectively; $\Psi(r)$ is a field map; $f_n$ is a chemical shift of an nth fat peak; and amplitude coefficient $\beta_n(TSL)$ is a relative amplitude of the nth fat peak.

7. The method of claim 6 wherein each amplitude coefficient $\beta_n(TSL)$ is approximated by a TSL-independent constant value.

8. The method of claim 6 further comprising:
performing a pre-calibration procedure to determine values for each amplitude coefficient $\beta_n(TSL)$.

9. The method of claim 1 wherein the region of interest comprises a tissue of a patient.

10. A magnetic resonance imaging (MRI) system comprising:
an MRI apparatus having a magnet, a gradient coil, and one or more radiofrequency (RF) coils; and
a computer communicably coupled to the MRI apparatus, the computer having a processor, a memory, and a user interface, the processor being configured to:
apply a magnetization prep sequence that includes an adiabatic continuous-wave constant-amplitude spin-lock (ACCSL) pulse sequence;
perform an acquisition sequence to acquire a data set wherein the acquisition sequence incorporates a Dixon acquisition method;
generate a source image from the data set; and
analyze the source image using a Dixon analysis method to generate a water image and a fat image.

11. The system of claim 10 wherein the processor is further configured to:
determine, based on at least the water image, a spatial distribution of a spin-lock based imaging biomarker for each of a plurality of locations within a region of interest.

12. The system of claim 11 wherein the spin-lock based imaging biomarker is T1rho.

13. The system of claim 10 wherein the ACCSL pulse sequence includes an adiabatic half passage (AHP), a constant-amplitude spin-lock radiofrequency (RF) pulse having a spin-lock time, and a reverse AHP, wherein an RF amplitude of the AHP and the reverse AHP is equal to a spin-lock amplitude.

14. The system of claim 10 wherein the Dixon acquisition method is a 3-point Dixon method.

15. The system of claim 10 wherein the processor is further configured such that analyzing the data set to generate a water image and a fat image includes modeling the source image as:

$$s(r, TE, TSL) = \left(\rho_w(r, TSL) + \rho_f(r, TSL) \sum_{n=1}^{N_p} [\beta_n(TSL) \cdot e^{j2\pi f_n TE}]\right) \cdot e^{j2\pi \Psi(r) TE},$$

wherein $s(r, TE, TSL)$ is a source image element acquired at a location r with spin-lock time TSL and echo time TE; $\rho_w(r, TSL)$ and $\rho_f(r, TSL)$ are the water and fat images, respectively; $\Psi(r)$ is a field map; $f_n$ is a chemical shift of an nth fat peak; and amplitude coefficient $\beta_n(TSL)$ is a relative amplitude of the nth fat peak.

16. The system of claim 15 wherein each amplitude coefficient $\beta_n(TSL)$ is approximated by a TSL-independent constant value.

17. The system of claim 15 further comprising:
performing a pre-calibration procedure to determine values for each amplitude coefficient $\beta_n(TSL)$.

18. The system of claim 11 wherein the region of interest comprises a tissue of a patient.

\* \* \* \* \*